United States Patent
Liu et al.

(10) Patent No.: US 9,327,283 B2
(45) Date of Patent: May 3, 2016

(54) DEVICE AND METHOD FOR ANALYZING ANALYTE IN LIQUID SAMPLES

(75) Inventors: Wei Liu, Zhejiang (CN); Andrew P. Phelan, Bedford (GB); Zhong-Qi Jin, Zhejiang (CN); Ying-An Zhan, Zhejiang (CN); Shuang Yu, Zhejiang (CN); Fu-Qiang Huang, Zhejiang (CN); Li Wang, Zhejiang (CN); Yin-Fei Wu, Zhejiang (CN); Jian Zou, Zhejiang (CN)

(73) Assignee: Alere Switzerland GmbH, Zug (CH)

( * ) Notice: Subject to any disclaimer, the term of this patent is extended or adjusted under 35 U.S.C. 154(b) by 681 days.

(21) Appl. No.: 13/394,759

(22) PCT Filed: Jul. 9, 2010

(86) PCT No.: PCT/CN2010/001020
§ 371 (c)(1),
(2), (4) Date: Apr. 17, 2012

(87) PCT Pub. No.: WO2011/003281
PCT Pub. Date: Jan. 13, 2011

(65) Prior Publication Data
US 2012/0192628 A1  Aug. 2, 2012

(30) Foreign Application Priority Data

Jul. 9, 2009  (CM) ...................... 2009 2 0124328 U
Jul. 9, 2009  (CN) .......................... 2009 1 0100353
Jul. 9, 2009  (CN) ...................... 2009 2 0124329 U
Sep. 7, 2009  (CN) .......................... 2009 1 0152616

(51) Int. Cl.
*B01L 3/00* (2006.01)

(52) U.S. Cl.
CPC ........... *B01L 3/502* (2013.01); *B01L 2200/025* (2013.01); *B01L 2200/0689* (2013.01);
(Continued)

(58) Field of Classification Search
CPC ............ B01L 3/502; B01L 2300/0681; B01L 2400/0478; B01L 2300/047; B01L 2200/141; B01L 2400/0481; B01L 2300/044; B01L 2300/087; B01L 2400/0406; B01L 2300/0825; B01L 3/5635; B01L 2300/0877
USPC ................. 73/64.56, 863.23, 864.61, 864.81; 422/68.1, 527, 547, 559, 522, 401, 422/504, 513
See application file for complete search history.

(56) References Cited

U.S. PATENT DOCUMENTS 5,016,644 A * 5/1991 Guirguis ........................ 600/584
5,215,102 A * 6/1993 Guirguis ........................ 600/584
(Continued)

FOREIGN PATENT DOCUMENTS

CN         2458614 Y        11/2001
CN         2724003 Y         9/2005
(Continued)

*Primary Examiner* — Hezron E Williams
*Assistant Examiner* — Marrit Eyassu
(74) *Attorney, Agent, or Firm* — DLA Piper LLP (US)

(57) ABSTRACT

A device and a method for analyzing an analyte in a liquid sample are provided. The device comprises a detecting chamber included in a detection device for containing a detecting element; a liquid sample transferring chamber; and a film with small pores disposed between the detecting chamber and liquid sample transferring chamber. When the detection device is inserted into a liquid sample collecting chamber, the liquid sample in the collecting chamber enters the liquid sample transferring chamber but can not enter the detecting chamber via the film with small pores. When a piston is inserted into the liquid sample transferring chamber, the piston forces a part of liquid sample in the liquid sample transferring chamber to enter the detecting chamber via the film with small pores. Using the device and the method can determine an analyte in a sample quantitatively and can complete the detection in one step.

19 Claims, 13 Drawing Sheets

(52) U.S. Cl.
CPC ...... *B01L2200/141* (2013.01); *B01L 2300/027* (2013.01); *B01L 2300/047* (2013.01); *B01L 2300/048* (2013.01); *B01L 2300/0609* (2013.01); *B01L 2300/0681* (2013.01); *B01L 2300/0825* (2013.01); *B01L 2400/0478* (2013.01)

(56) References Cited

U.S. PATENT DOCUMENTS

| | | | |
|---|---|---|---|
| 5,352,410 A * | 10/1994 | Hansen | A61B 10/007 422/419 |
| 6,680,027 B2 | 1/2004 | Kang et al. | |
| 7,534,397 B2 | 5/2009 | Dumitrescu | |
| 7,758,815 B2 | 7/2010 | Hartselle | |
| 7,850,915 B2 * | 12/2010 | Morozov et al. | 422/68.1 |
| 7,947,186 B2 * | 5/2011 | Soares et al. | 210/782 |
| 2003/0021736 A1 | 1/2003 | Kang et al. | |
| 2003/0022392 A1 * | 1/2003 | Hudak | 436/518 |
| 2005/0048670 A1 * | 3/2005 | Wu et al. | 436/180 |
| 2006/0029517 A1 | 2/2006 | Hartselle | |
| 2008/0138251 A1 | 6/2008 | Dumitrescu | |
| 2008/0318342 A1 * | 12/2008 | Durack et al. | 436/526 |
| 2011/0165022 A1 * | 7/2011 | Meathrel et al. | 422/68.1 |

FOREIGN PATENT DOCUMENTS

| | | |
|---|---|---|
| CN | 2763795 Y | 3/2006 |
| CN | 1842299 A | 10/2006 |
| CN | 1950688 A | 4/2007 |
| CN | 2011/77628 Y | 1/2009 |
| WO | WO 2005/119253 A1 | 12/2005 |

\* cited by examiner

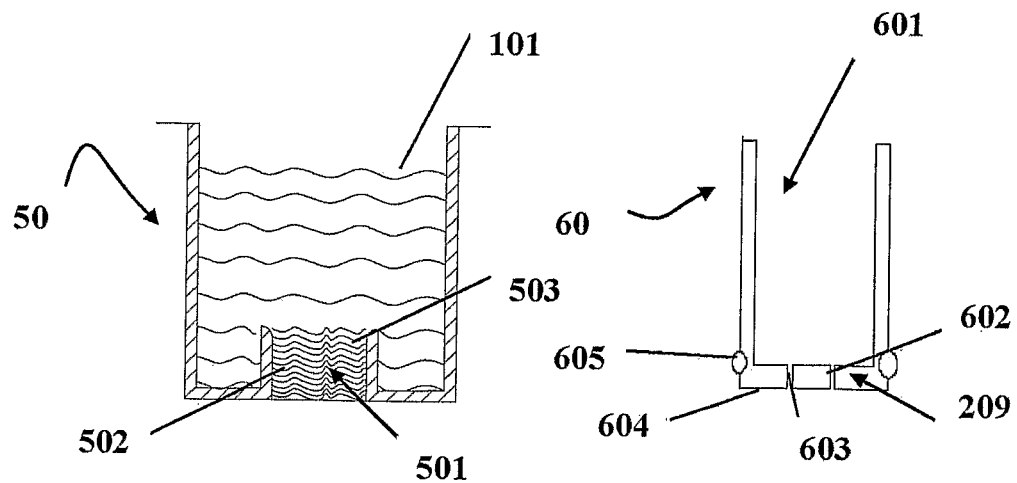
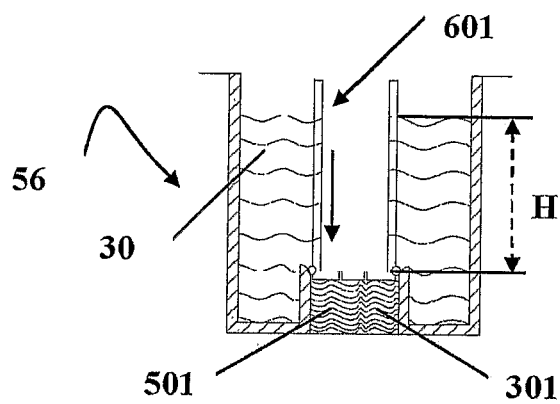
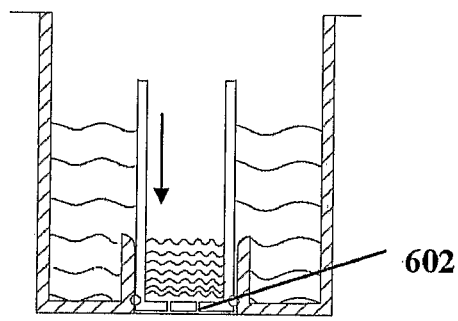

DEVICE AND METHOD FOR ANALYZING ANALYTE IN LIQUID SAMPLES

CROSS REFERENCE TO RELATED APPLICATIONS

This application is a 35 USC §371 National Stage application of International Application No. PCT/CN2010/001020 filed Jul. 9, 2010; which claims the benefit under 35 USC §119(a) to China Patent Application No. CN200910152616.X filed Sep. 7, 2009, China Patent Application No. CN200910100353.8 filed Jul. 9, 2009, China Patent Application No. CN200920124329.3 filed Jul. 9, 2009 and China Patent Application No. CN200920124328.9 filed Jul. 9, 2009. The disclosure of each of the prior applications is considered part of and is incorporated by reference in the disclosure of this application.

TECHNICAL FIELD

The present invention relates to the field of collecting liquid samples, particularly, the present invention relates to the field of collecting a liquid sample and detecting an analyte in the sample, especially for determining whether the sample contains metabolites of drugs and abused substances, or for rapidly diagnosing and detecting pregnancy.

BACKGROUND

Recently, detection devices are widely used for detecting analytes, such as indicating materials of drug abuse or diseases, in human fluids including urine, saliva, or blood. The traditional detection devices typically need to have a container for collecting a liquid sample, and to have a detecting element inserted into the liquid sample and subsequently taken out so that the testing results shown thereon can be read (by eyes or instruments). However, there is a risk that the operator may be contaminated by the sample during such a process. Furthermore, besides professionals, the detection devices are also widely used by ordinary people in places such as at home. Therefore, there are demands for detection devices that not only can be operated more easily, but also provides more accurate detection results.

SUMMARY OF INVENTION

The present invention relates to a detection device for detecting an analyte in a liquid sample. Such a device can take samples quantitatively and detects whether the analyte is contained in the sample. The device comprises a detecting chamber for accepting a detecting element, a liquid sample transferring chamber for transferring a certain amount of sample into the detecting chamber, and a film of small pores disposed between the detecting chamber and the liquid sample transferring chamber. When the detecting device is inserted into a liquid sample collecting chamber, the liquid sample in the collecting chamber enters the liquid sample transferring chamber, but it cannot enter the detecting chamber via the said film of small pores, and when a piston is inserted into the liquid sample transferring chamber, the piston can force a part of the liquid sample in the transferring chamber to enter the detecting chamber via the small pores on the film.

In some preferable embodiments, the small pores on the film can be so configured that the liquid surface tension at the small pores can prevent the liquid sample from freely entering the detecting chamber; when the pressure difference between the transferring chamber and the detecting chamber is less than or equal to the liquid surface tension at the small pores, the liquid sample in the transferring chamber therefore cannot freely enter the detecting chamber via the small pores of the film, and when the pressure difference between the transferring chamber and the detecting chamber become greater than the liquid surface tension at the small pores, the liquid sample in the transferring chamber can be forced to enter the detecting chamber via the small pores. More preferably, the piston moving inside the transferring chamber can increase the pressure therein to that greater than the liquid surface tension at the small pores.

In some other preferable embodiments, there is a liquid channel between the liquid sample transferring chamber and the collecting chamber, and said liquid channel can be sealed by the piston after a part of liquid sample in the collecting chamber flows into the transferring chamber via the channel. Preferably, when the piston seals the liquid channel, the pressure inside the transferring chamber is less than or equal to the liquid surface tension at the small pores of the film between the detecting chamber and the liquid sample transferring chamber; more preferably, the piston has a first position and a second position in the transferring chamber; when at the first position, the piston can seal the liquid channel between the collecting chamber and the transferring chamber, there is a part of the liquid sample in the transferring chamber, but this liquid sample cannot enter the detecting chamber via the small pores of the film, and when moving from the first position to the second position, the piston can then force the liquid sample in the transferring chamber to enter the detecting chamber via the small pores of the film.

In other preferable embodiments, the piston can be located within the liquid sample collecting chamber. The transferring chamber and the detecting chamber can be connected as one piece, or more preferably, the transferring chamber, the detecting chamber, and the film of small pores can be constructed as one piece through injection molding. Furthermore, the film can contain one or more small pores, and the small pores of the film can have diameters between 0.1 and 5 millimeters In yet other preferable embodiments, the film of small pores can be a hydrophobic film. Such a hydrophobic film can comprise a hydrophilic film whereon hydrophobic reagent is treated; it can also comprise glass fibers, polyester film, or acetic fiber film. The pore sizes of such a hydrophobic film can be between 0.1 and 100 microns. Moreover, the hydrophobic film can have a gas permeating rate of 10-800 cubic inches/minute/square inch.

Another aspect of the invention relates to a similar detection device for analyzing an analyte in a liquid sample, which comprises a detecting chamber for accepting a detecting element, with a film of small pores disposed at one end of the detecting chamber, and a liquid sample transferring chamber that is located within a liquid sample collecting chamber. In such a device, when the detecting chamber is inserted into the liquid sample collecting chamber, the liquid sample in the collecting chamber cannot enter the detecting chamber via the small pores of the film, but when the detecting chamber is inserted into the transferring chamber located within the collecting chamber, a part of the liquid sample inside the transferring chamber can be forced to enter the detecting chamber via the film of small pores.

In some preferable embodiments, the film of small pores can be integrated into the end of the detecting chamber. The transferring chamber can be located on the bottom of the collecting chamber and protrudes upwardly; preferably, the transferring chamber opens upwardly at the end so that a part of the liquid sample in the collecting chamber can enter the transferring chamber through the opening, and the detecting chamber can seal the opening when it is inserted into the transferring chamber. More preferably, the small pores of the film are so configured that the liquid surface tension at the pores can prevent the liquid sample from freely entering the detecting chamber; when the detecting chamber seals the opening of the transferring chamber, the pressure difference between the transferring chamber and the detecting chamber is less than or equal to the liquid surface tension at the small pores, and when the detecting chamber moves along inside the transferring chamber, the pressure difference between the transferring chamber and the detecting chamber increases to that greater than the liquid surface tension at the small pores, and thus, the liquid sample in the transferring chamber is forced to enter the detecting chamber via the small pores.

In some other preferable embodiments, the film of small pores and the detecting chamber can be constructed as one piece through injection molding. The film can contain one or more small pores, and the pores can have diameters of between 0.1 and 5 millimeters. Preferably, the film of small pores can be made of plastic, the pores of such a plastic film can have diameters of between 0.2 and 1 millimeter, and the thickness of the film can be between 0.5 and 2.0 millimeters.

In yet other preferable embodiments, the film of small pores can be a hydrophobic film. Such a hydrophobic film can comprise a hydrophilic film whereon hydrophobic reagent is treated; it can also comprise glass fibers, polyester film, or acetic fiber film. The pore sizes of such a hydrophobic film can be between 0.1 and 100 microns. Moreover, the hydrophobic film can have a gas permeating rate of 10-800 cubic inches/minute/square inch.

Another aspect of the invention relates to a detection kit that can adopt for example the above detection devices. Such a detection kit can comprise a detection device that has a detecting chamber, a liquid sample transferring chamber, a film of small pores that is disposed between the transferring chamber and the detecting chamber, and a liquid sample collecting chamber comprising a piston for inserting into the transferring chamber. When in use, the transferring chamber is inserted into the collecting chamber, the liquid sample in the collecting chamber then can flow into the transferring chamber, but the liquid sample cannot enter the detecting chamber via the film of small pores, and when the pistol is inserted into the transferring chamber, a part of liquid sample in the transferring chamber can be forced to enter the detecting chamber via the film of small pores. Preferably, the piston is located on the bottom of the collecting chamber and protrudes upwardly.

In some preferable embodiments, the small pores of the film are so configured that the liquid surface tension at the pores can prevent the liquid sample from freely entering the detecting chamber; when the pressure difference between the transferring chamber and the detecting chamber is less than or equal to the liquid surface tension at the small pores, the liquid sample in the transferring chamber cannot enter the detecting chamber via the small pores, and when the pressure difference between the transferring chamber and the detecting chamber is greater than the liquid surface tension at the small pores, the liquid in the transferring chamber can then enter the detecting chamber via the small pores.

In other preferable embodiments, the liquid sample transferring chamber further comprises a liquid channel allowing liquid to freely pass through, and said liquid channel is sealed by the piston after a part of liquid sample in the collecting chamber flows into the transferring chamber via the channel. Preferably, the pressure inside the transferring chamber is less than or equal to the liquid surface tension at the small pores when the piston seals the liquid channel; more preferably, the piston has a first position and a second position in the transferring chamber; when at the first position, the piston seals the liquid channel, the transferring chamber contains a part of liquid sample from the collecting chamber, but the liquid sample cannot enter the detecting chamber via the film of small pores because the pressure difference between the transferring chamber and the detecting chamber is smaller or equal to the liquid surface tension at the pores; when moving from the first position to the second position, the piston increase the pressure inside the transferring chamber and force a part of the liquid sample therein to enter the detecting chamber via the film of small pores.

In yet other preferable embodiments, the film of small pores can be a hydrophobic film. Such a hydrophobic film can comprise a hydrophilic film whereon hydrophobic reagent is treated; it can also comprise glass fibers, polyester film, or acetic fiber film. The pore sizes of such a hydrophobic film can be between 0.1 and 100 microns. Moreover, the hydrophobic film can have a gas permeating rate of 10-800 cubic inches/minute/square inch.

Another aspect of the invention relates to a method of analyzing an analyte in a liquid sample by using for example the above devices or kits. The method comprises inserting a detecting device into a liquid sample collecting chamber, and allowing the liquid sample in the collecting chamber to enter a liquid sample transferring chamber of the detecting device via a liquid channel, but not allowing the liquid sample to enter a detecting chamber of the detecting device via a film of small pores disposed between the detecting chamber and the transferring chamber, and subsequently, inserting a piston into the liquid sample transferring chamber to force the liquid sample in the transferring chamber to enter the detecting chamber via the film of small pores. Preferably, the liquid sample and a detecting element disposed in the detecting chamber can be in contact. More preferably, the piston can be located within the collecting chamber; the liquid sample transferring chamber, the detecting chamber, and the film of small pores can be connected as one piece, and the collecting chamber and the piston can be connected as one piece.

In some preferable embodiments of the method, the piston has a first position and a second position in the transferring chamber; when at the first position, the piston seals the liquid channel, but the liquid sample in the transferring chamber cannot freely enter the detecting chamber via the film of small pores; and, moving the piston from the first position to the second position allows a part of liquid sample in the transferring chamber to enter the detecting chamber via the film of small pores.

In other preferable embodiments, the small pores of the film are so configured that the liquid surface tension at the small pores can prevent the liquid sample from freely entering the detecting chamber; by allowing the pressure difference between the transferring chamber and the detecting chamber to be less than or equal to the liquid surface tension at the small pores, the liquid sample in the transferring chamber is prevented from entering the detecting chamber via the small pores, and conversely, by allowing the pressure difference between the transferring chamber and the detecting chamber to be greater than the liquid surface tension at the small pores, a part of the liquid sample in the transferring chamber can be forced to enter the detecting chamber via the small pores.

In yet other preferable embodiments of the method, the piston is allowed to move along inside the transferring chamber to increase the pressure therein; more preferably, the piston is not allowed to move backward after entering and moving forward in the transferring chamber to force a part of liquid sample therein to enter the detecting chamber via the film of small pores.

In all the above aspects and their embodiments, the detecting chamber in the device, detection kit or method can include a detecting element; preferably, it can have a reading device for reading the detecting results of the detecting element; more preferably, the detecting element can be a lateral flow reagent strip.

In sum, the present invention can complete the detection of an analyte in a liquid sample completed in one step, thus greatly simplifying the operation procedure. It does not cause any environmental contamination and can be operated conveniently and swiftly, and thus, is very suitable for home use. In addition, the present invention is capable of quantitatively detecting a liquid sample, which improves the accuracy and sensibility of the detection.

BRIEF DESCRIPTION OF THE FIGURES

FIG. 3 is an illustration of the operating principle of some other specific embodiments of the present invention.

REMARKS OF THE REFERENCE SIGNS

Figure 1A:
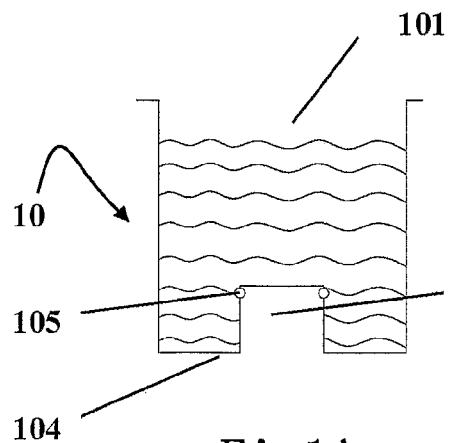
FIG. 1 is an illustration of the operating principle of some specific embodiments of the present invention in cases of having sufficient liquid sample.

Detection device 20, 60, 71; detection kit 70, 90, 56; detecting element 40, 717; lid 711; detecting chamber 202, 601, 716, 171; film of small pores 209, 7111; small pores 203, 205, 713, 714; inner surface of small pores 2003; cone-shaped small pore 713, inverse cone-shaped small pore 714; transferring chamber 208, 172; piston chamber 201, 501, 712; liquid channel or piston chamber opening 503, 204, 715; one end of the detecting chamber 604; result displaying window 710; piston 102, 722; opening of the collecting chamber 723; collecting chamber 721, 101; bottom 724, 104; reading device 718; sealing ring 105, 726; barrier element 719; screw thread 727; hydrophobic film of small pores 170, opening 173.

DETAILED DESCRIPTION

In the following detailed descriptions, the figures and the corresponding descriptions only illustrate some exemplary embodiments of the present invention. Any other specific embodiments of the present invention that can be carried out without violating the scope of protection defined in the claims are not excluded.

One aspect of the invention provides a detection device for detecting an analyte in a liquid sample. The device can detect and test liquid sample without contaminating other remaining liquid samples. And the detection can be completed in one step without involving complicated operational steps. The detection device 20 comprises: a detecting chamber 202 for accepting a detecting element, a liquid sample transferring chamber 208, and a film of small pores 209 separating the detecting chamber and the liquid sample transferring chamber; wherein when the detecting device is inserted into a liquid sample collecting chamber 101, the liquid sample 30 in the collecting chamber 101 flows into the liquid sample transferring chamber 208, but cannot enter the detecting chamber via the porous film 209; and when a piston 102 is inserted into the liquid sample transferring chamber 208, the piston 102 forces a part of the liquid sample 301 in the transferring chamber 208 to enter the detecting chamber 202 via said film of small pores 209.

Figure 1B:
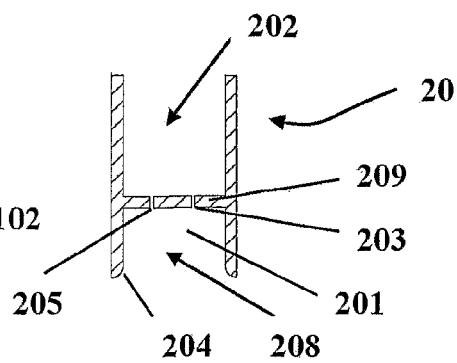
Figure 1C:
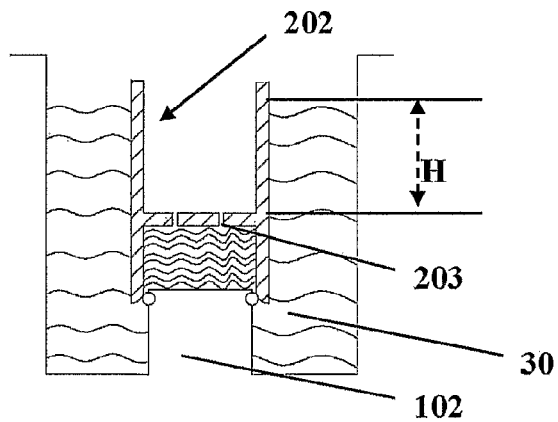
Figure 1D:
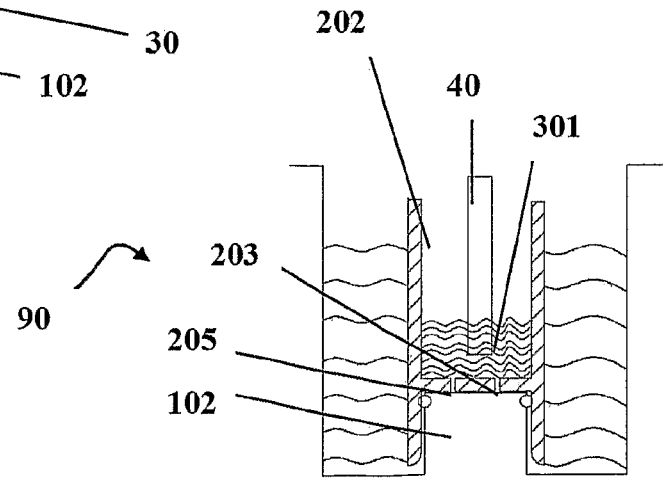

FIG. 1A-1D shows a specific embodiment of the invention. Detailed explanations are given here below. FIG. 1A shows a liquid sample collecting device 10 in one embodiment of the invention, which comprises a liquid sample collecting chamber 101 formed by side wall and bottom 104, with one end being open for accepting a liquid sample and another end closed. A piston 102 is located on the bottom 104 of the collecting chamber and protrudes upwardly. Fig IB shows a detecting chamber 202 included in the detecting device 20 in one specific embodiment of the invention, such a detecting chamber is used to contain a detecting element 40 and to accept liquid sample from the transferring chamber; further, Fig IB shows a liquid sample transferring chamber 208, and a film with pores 209 that is disposed between the detecting chamber 202 and the liquid sample transferring chamber 208, with the film separating the detecting chamber 202 and the liquid sample transferring chamber 208. The transferring chamber in FIG. 1B can specifically be a piston chamber 201, which has an opening at one end, and this end provides a liquid channel 204 through which the liquid sample can enter the piston chamber; the other end of the piston chamber is sealed by a film having small pores, such as small pores 203 and 204 shown in FIG. 1B that are used to connect the piston chamber and the detecting chamber. When in use, the detecting device is inserted into the collecting chamber 101, the liquid sample in the collecting chamber enters the transferring chamber via the channel 204 but cannot enter the detecting chamber 202 via the film 209. When the piston 102 in the collecting chamber is inserted into the transferring chamber 208, specifically the piston chamber 201 in FIG. 1, the piston forces a part of liquid sample to enter the detecting chamber 202 via small pores 203, 205 on the film 209, as shown in FIG. 1C. In a preferable manner, if the detecting chamber comprises a detecting element 40, the liquid sample entering the detecting chamber contacts the detecting element for assaying and detecting, as shown in FIG. 1D.

In some other preferable embodiments, the size and shape of the small pores can be configured such that the liquid surface tension becomes apparent at the small pores, such as by setting the inner diameter of the small pores to be 0.5 millimeter. When an amount of liquid sample is collected in the collecting chamber, as shown in Fig A, a large amount of liquid sample is collected in the collecting chamber. Then, the detecting device 20 is inserted into the collecting chamber 101, while approaching to the piston 102, a part of liquid sample in the collecting chamber enters the transferring chamber 208 or, more specifically the piston chamber 201, via the channel 204, and air in the piston chamber is expelled outside the transferring chamber via the small pores 203 or 205. Since the detecting chamber is connected with air, the pressure inside the transferring chamber 208 or the piston chamber 201 equals to that in the detecting chamber 202 and the pressure difference is almost zero, less than the predetermined liquid surface tension at the small pores. The transferring chamber or piston chamber moves downward continuously and the air therein is expelled out accordingly; eventually, the entire transferring chamber 208 or piston chamber 201 is full of liquid sample 30 and liquid is in contact with air at where the small pores locate. Because of the presence of the small pores, the liquid generates apparent liquid surface tension at the small pores. When piston chamber 201 or transferring chamber 208 moves downward continuously, the liquid level in the chambers goes down eventually to below the liquid level of the collecting chamber 101 (when there are sufficient or large amount of liquid sample). When the transferring chamber or piston chamber goes downward continuously, the opening of the chambers, i.e., the channel 204, cooperates with the piston 102 and is sealed by the piston. The piston seals the channel 204 and inhibits more liquid sample in the collecting chamber from entering the piston chamber, and the piston is now positioned at a so-called first position inside the piston chamber. At this time, there is a level difference H between two liquid surfaces, as shown in FIG. 1C, which increases the pressure under liquid surface of small pore 203 or 205. However, since small pores are configured to have sizes and shapes, the liquid surface tension generated by the interaction between the liquid and air at the pores can be configured to be greater than the pressure generated by the liquid surface level difference H. At this time, the liquid sample in the transferring chamber cannot enter the detecting chamber via the small pores 203 and 205. When the transferring chamber 208 or piston chamber 201 moves downward continuously from the first position to a so-called second position, the piston 102 in the collecting chamber moves deeper in the chambers so as to increase the pressure below the surface of the small pores, which breaks the liquid surface tension configured by the small pores and allows the liquid sample in the transferring chamber or piston chamber to enter the detecting chamber via the small pores 203 or 205 and to react with the detecting element 202. At this time, the piston is positioned at the second position in the piston chamber.

In some other specific embodiments, after the piston chamber contains a part of the liquid sample, the piston and the piston chamber can be kept sealed during the process that the piston 101 seals the liquid channel 204 and moves inside the piston chamber, which can prevent the liquid sample in the collecting chamber from entering the piston chamber and achieves the purpose of sampling quantitatively. For a better sealing effect, one or more plastic, rubber or silicon sealing rings such as "O" ring 105 can be disposed at the outside surface of the piston, as shown in FIG. 1A. It is of course possible that the piston does not seal the channel 204 but moves along the piston chamber quickly such that the piston presses the liquid in the piston chamber to generate an instant pressure. Such an instant pressure may break the inherent liquid surface tension configured by the small pores and to allow the liquid in the piston chamber to enter the detecting chamber.

Besides the above specific embodiments, the film of small pores having desired property can be freely selected. For example, films having micro-pores, such as nitric acid fiber films, nylon films or filtering paper, glass fibers and the like can be selected. It can also be plastic sheets having micro holes.

In some other more preferable specific embodiments, the film of small pores can be hydrophobic film of small pores. The "hydrophobic film of small pores" mentioned here refers to those are composed of or consist of materials that are hydrophobic materials or substantively hydrophobic materials; or the film of small pores consists of hydrophilic materials but the hydrophilic film becomes a hydrophobic film after treatment of hydrophobic reagents. The hydrophilic materials can be nitric acid fiber film, nylon film or filtering paper, glass fibers and the like, which become hydrophobic after treating the surfaces with hydrophobic reagent. Most of hydrophilic materials typically carry molecules of polar groups and have great affinity to water, which can absorb water molecules or are soluble to water. Hydrophobic molecules, however, tent to be non polar and therefore are soluble in neutral and non polar solutions (such as organic solvents). Hydrophobic molecules typically aggregate together in water, and water, when on surface of hydrophobic solution, will form a large contacting angle thereby forming blob. Such a film can be at least 20% hydrophobic, at least 30% or 50% hydrophobic, preferably 60% or 70% hydrophobic, and most preferably 80% to 90% hydrophobic. The small pores on the film can be formed simultaneously when the film is formed, and can also be designed freely during processing or production. The size of the small pores can be from 0.1 to 100 microns, can be 3 to 80 microns, 4 to 50 microns, and can also be from 8 to 15 microns; and the size of the small pores can be uniform or variable within a range. For example, the small pores can have a uniformed size of 20, 30, 8 or 25 microns, and it is also acceptable that 30% of small pores on the film have a size between 20 and 15 microns while the rest 70% being between 2 and 13 microns. The hydrophobic films can be hydrophobic nitric acid fiber films, hydrophobic nylon films or hydrophobic filtering paper, hydrophobic glass fibers or hydrophobic polyester films and the like. These films of small pores can be purchased directly from market such as from AHLSTROM FILTRATION LLC, www.ahlstrom.com, addressed at 42431-0030, Kentucky, U.S.A, (270) 821-0140, (270) 326-3290, Fax: post box 1410.

Figure 17:
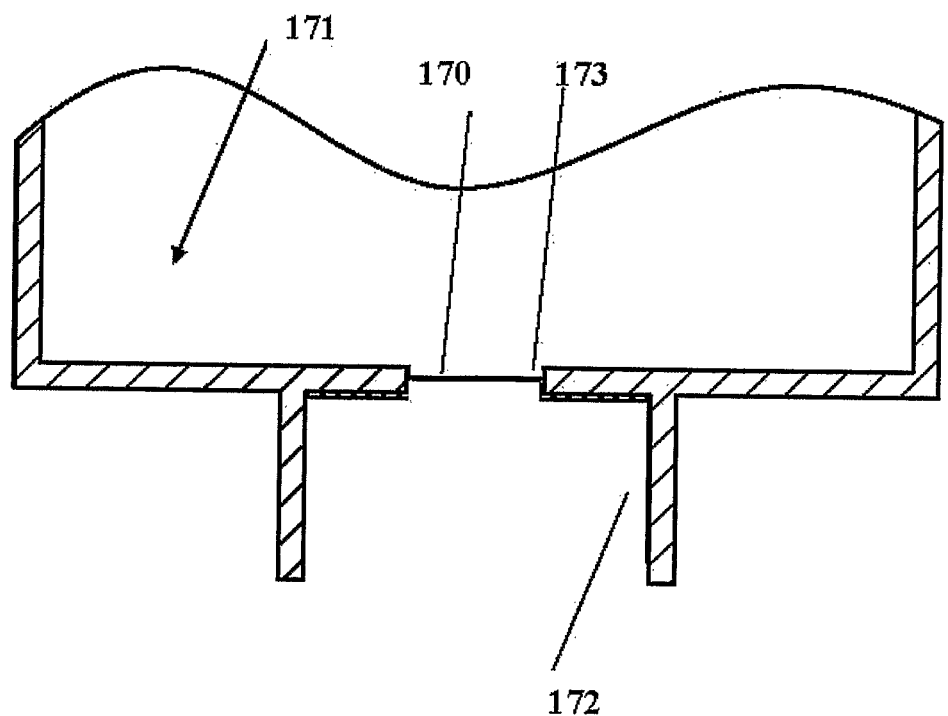
FIG. 17 is an enlarged view of the structure of parts of the detecting chamber and transferring chamber of the detecting device in a specific embodiment of the present invention.
Figures 18A, 18B, 18C, 18D:
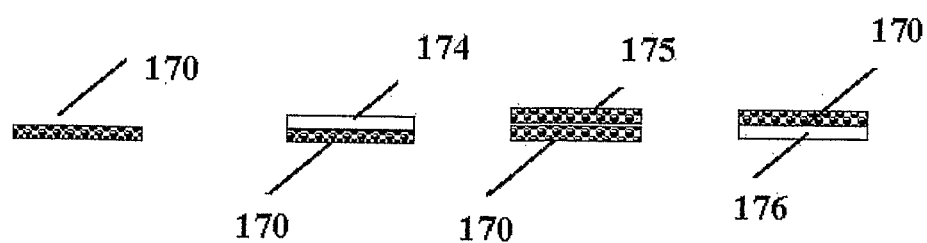
FIG. 18 is the combination manner of the hydrophobic films of small pores in different embodiments of the present invention.

In a specific embodiment as shown in FIGS. 17 and 18, FIG. 17 is an enlarged view of a part of structure of the detecting device in a specific example of the invention. Detecting chamber 171 and transferring chamber 172 share a common wall 177 whereon there opens a small pore 173 having a diameter of about 6 to 8 millimeters; a hydrophobic film 170 is adhered at where the small pore locates to separate the detecting chamber 171 and the transferring chamber 172. Preferably, to facilitate production, the hydrophobic film of small pores can be directly injection molded between the detecting chamber and the transferring chamber. For example, when producing the detecting device shown in FIG. 17, placing a slice of hydrophobic film of small pores in the mold, and injecting liquid plastic into the mold such that the hydrophobic film of small pores is injection molded between two chambers 171 and 172 as one step. Such a film can be a layer of hydrophobic film of small pores having a thickness of about 10 to 50 microns, a stretching intensity of 30 to 100 lb/inch, and a gas permeability of 1-800 cubic inch/min/ square inch (CFM) (Cubic feet per minute per square meter). Preferably, the gas permeability is 10-600 cubic inch/min/ square inch, 150-400 cubic inch/min/square inch, and can also be 150-400 CFM, and can further be 200-300 CFM. The film can also comprise two layers of films adhered together, with the one closer to the transferring chamber being a hydrophobic film of small pores 170 and the one closer to the detecting chamber being a hydrophilic film 174, as shown in FIG. 18B; or both layers are the hydrophobic films of small pores adhered together as 170, 175, shown in FIG. 18C. It can also be that a layer of hydrophobic reagent 176 is treated on the film of small pores 170, as shown in FIG. 18D.

The volume of the liquid sample entering the detecting chamber can be maintained relatively constant by using the hydrophilic film of small pores. When the shape of the detecting chamber is fixed, the liquid has a relatively fixed height in the detecting chamber, thereby detecting element for detecting whether the sample contains the analyte is immersed in the liquid sample in the detecting chamber with a relatively fixed depth, which significantly improves the detection accuracy and reduces errors between the products. Since the liquid sample absorbing part of the detecting element is immersed in the liquid with different depths, the detecting element does not absorb the same amount of liquid in a period of time, which might possibly affect the detection results of the entire detecting element. Especially when some electronic elements are used to read the result of the detecting element for the purpose of obtaining accurate detecting results, it is more preferable that the detecting elements are relatively stable and less interfered. In addition, changes of the liquid height in the detecting chamber caused by volume change have significant impact on the accuracy of some detecting indexes. For example, when detecting the tetrahydrocannabinol (THC) in urine sample, the same sample could have two contrary detecting results if the volume entering the detecting chamber is not relatively constant and varies in a wide range. Using a porous film can maintain the volume of the liquid entering the detecting chamber within a relatively constant range, possibly because this type of film comprises many fine micro-pores of sizes between 0.1 and 100 microns. When the detecting element is put into the collecting chamber, the liquid sample enters the transferring chamber because of the opening on the transferring chamber. The air inside the transferring chamber is expelled out via the micro-pores on the film while the liquid entering such that the entire transferring chamber is full of the liquid sample. However, the liquid cannot get into the detecting chamber via the micro-pores because of the hydrophobic property of the film contacting the liquid. When the piston is inserted into the transferring chamber, the liquid sample in the transferring chamber is forced to enter the detecting chamber via the micro-pores. Because of the presence of the plurality of such fine pores, it is readily to the liquid sample to enter the detecting chamber. When selecting the film, the gas permeability and stretching intensity are references. The gas permeability can be used to determine the ventilation property and the stretching intensity to determine the pressure to be loaded.

Figures 10, 11, 12:
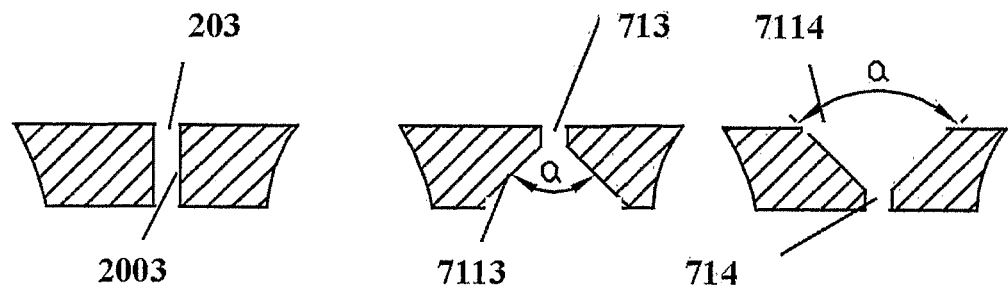
FIG. 10 is an enlarged view of the structure of the small pores in one specific embodiment.
FIG. 11 is an enlarged view of the structure of the small pores in another specific embodiment.
FIG. 12 is an enlarged view of the structure of the small pores in another specific embodiment.

In some other preferable embodiments, detecting chamber 202 and the transferring chamber 201 share a commonly wall, such as 209 on FIG. 1B, which separates the detecting chamber and the transferring chamber. Some small pores 203 or 205 are located on the wall 209 such that the detecting chamber and the transferring chamber can communicate. In a more preferable manner, the detecting device is injection molded as one step, and the common separating wall 209 is a plastic sheet having a thickness of 1.5 millimeter, and some small pores are disposed on the plastic sheet. In some other embodiments, the small pores on the film can be configured to adjust the liquid surface tension at the pores, such as changing the inner diameter, the depth, the shape of the small pores or the combination of these features. There may be one or more such small pores, such as two, three, four, five or more having diameters from 1-5 millimeters, such as 0.1, 0.2, 0.3, 0.4, 0.5, 0.8, 0.9, 1, 2, 3, 4, 5 or 6 millimeters, and in shapes of cylinder, cone or any other shapes. The small pores may have a thickness of 0.1-10 millimeters, such as 0.1, 0.2, 0.5, 1.0, 1, 3, 5, 7, 9, 2, 4 or 6 millimeters. In one specific embodiment, such as shown in FIGS. 10-12, the small pore is a cylinder 203 having an inner diameter of 0.5 millimeter and a depth of 1.5 millimeter; or a cone small pore 713, as shown in FIG. 11; or an inversed cone small pore 714, as shown in FIG. 12. There are many ways to change the size, shape or depth of the small pores; for example, it can be achieved by selecting different film materials, such as membrane, filtering paper and glass fibers having micro-pores. There are also many ways to separate the detecting chamber and the transferring chamber. For example, to mold a hollow cylinder having openings at both ends, and to dispose a layer of film having micro-pores such as a filtering paper of a thickness of 1.5 millimeters in the middle of the cylinder, the layer of the film then separates the cylinder into two chambers, a detecting chamber 202 and a transferring chamber 201.

Figures 2A, 2B:
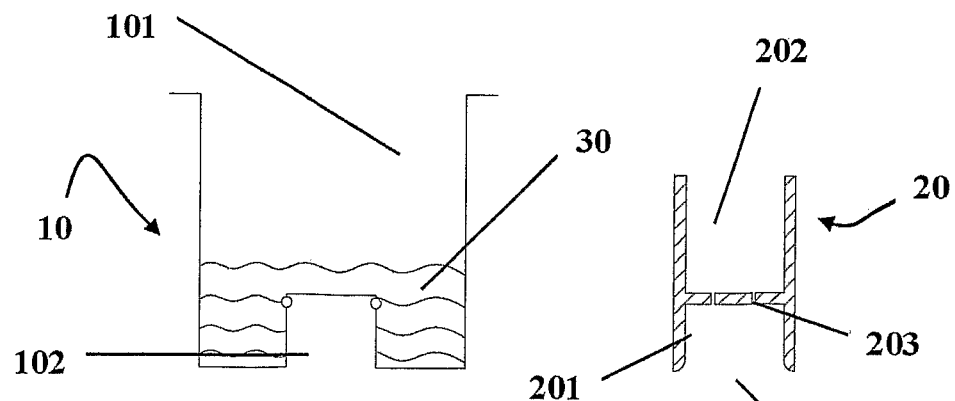
FIG. 2 is a longitudinal section view of the operating principle of some other specific embodiments of the present invention.
Figure 2C:
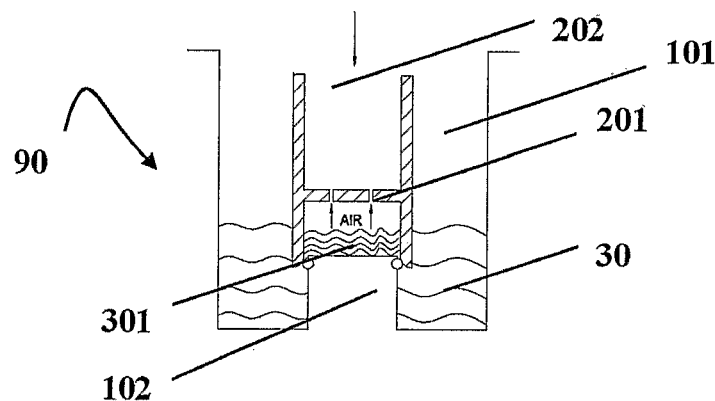
Figure 2D:
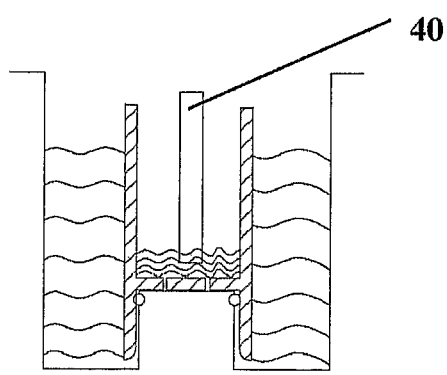
Figure 4:
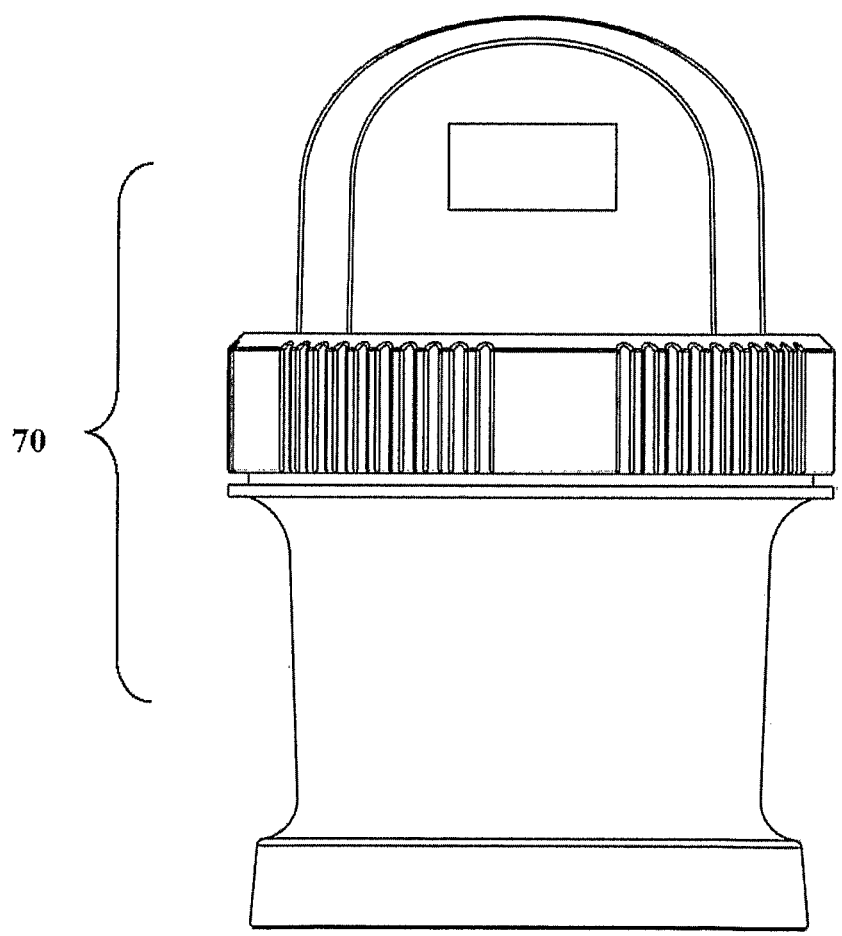
FIG. 4 is an outside view of a detection kit of one specific embodiment of the invention.

FIG. 2A-2D exhibits another specific embodiment of the invention, which is explained in detail here below. FIG. 2A exhibits a liquid sample collecting device 10 in a specific embodiment of the invention, which comprises a liquid sample collecting chamber 101 formed by side wall and bottom, with one end opened for accepting liquid sample and another end closed. A piston 102 is located at the bottom of the collecting chamber and protrudes upwardly. FIG. 1B shows a detecting device 20 in one specific embodiment of the invention, which comprises a detecting chamber 202 for containing a detecting element 20 and accepting liquid sample from the transferring chamber; and a piston chamber 201 that is eventually a transferring chamber; a layer of filtering paper 209 is disposed between the detecting chamber 202 and the piston chamber 201 for separating the detecting chamber and the liquid sample transferring chamber. When the collecting chamber 101 contains less liquid sample, the piston chamber 201 is partially filled with liquid sample when the detecting part 20 is inserted into the collecting chamber, and air in the piston chamber or transferring chamber is expelled out from the chamber via the micro-pores on the filtering paper, the liquid surface level in the piston chamber equals to that in the collecting chamber, and the pressure inside the piston chamber equals to that in the detecting chamber and the pressure difference therebetween is zero, as shown in FIG. 2C. When the detecting device moves downward continuously, the piston seals the liquid channel 204 to prevent the liquid volume in the piston chamber 201 from further increase. The piston chamber further moves downward continuously, and the piston forces the liquid inside the piston chamber to move relatively upward, the remaining air in the piston chamber is therefore excelled out from the chamber via the filtering paper 209. When the piston moves further into the piston chamber, it pushes the liquid inside the piston chamber to enter the detecting chamber 202 via the micro-pores on the filtering paper.

Figure 5:
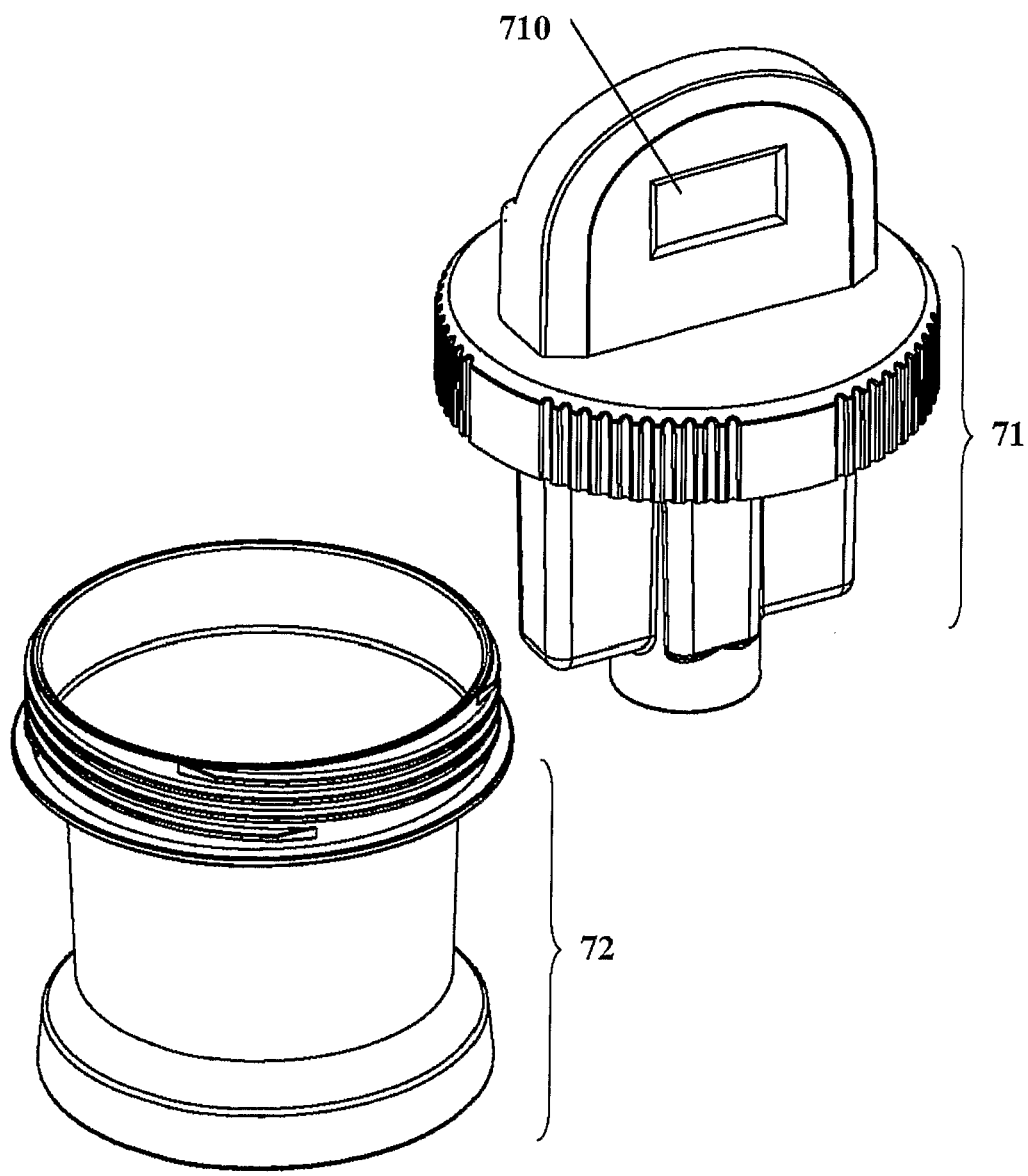
FIG. 5 is an exploded view of the structure of the detection kit shown by FIG. 4.
Figure 6:
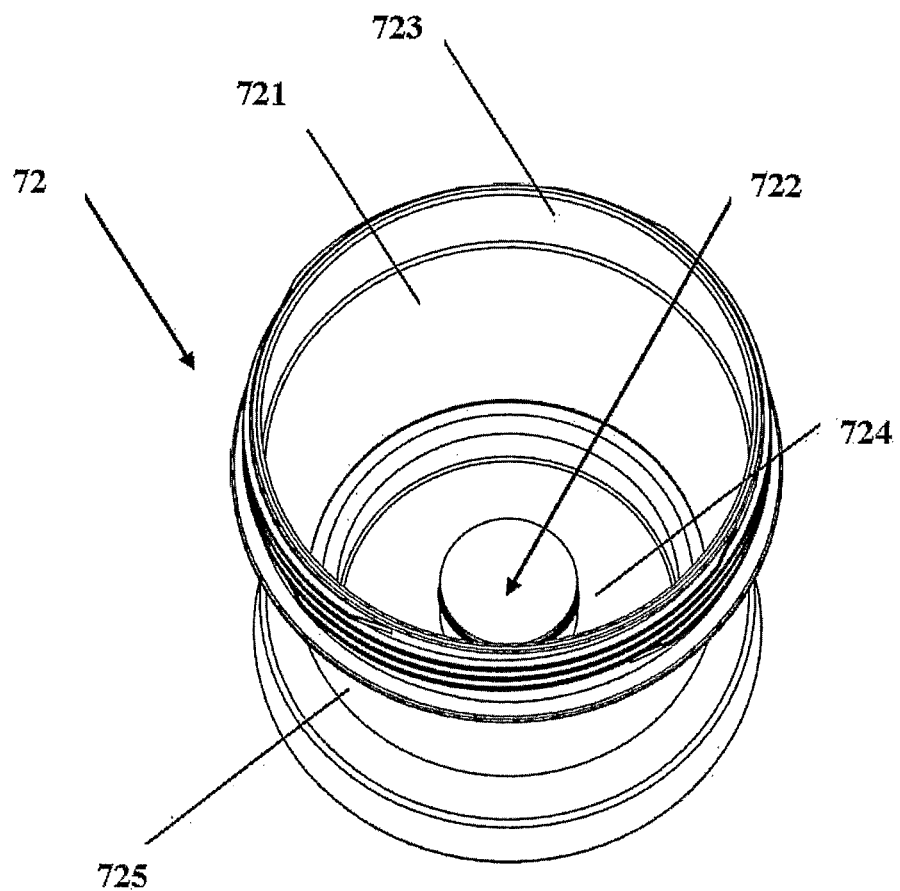
FIG. 6 is a perspective view of the structure of the collecting device shown by FIG. 4.
Figure 7:
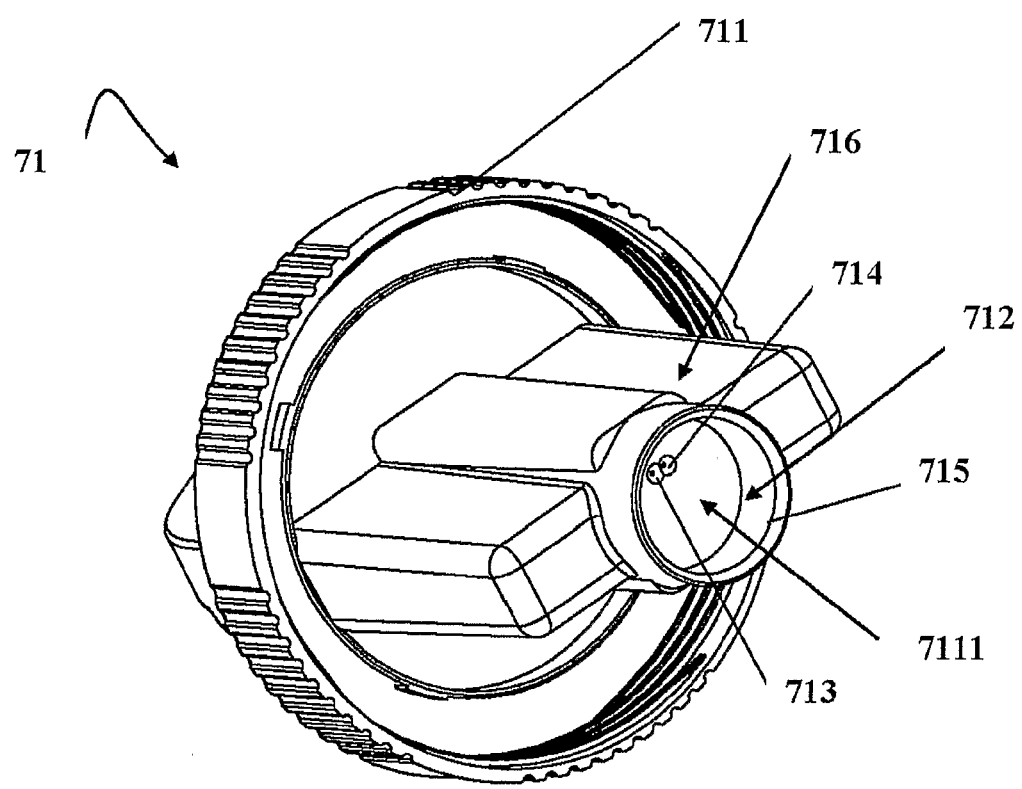
FIG. 7 is a perspective view of the structure of the detecting device shown by FIG. 4.
Figure 13:
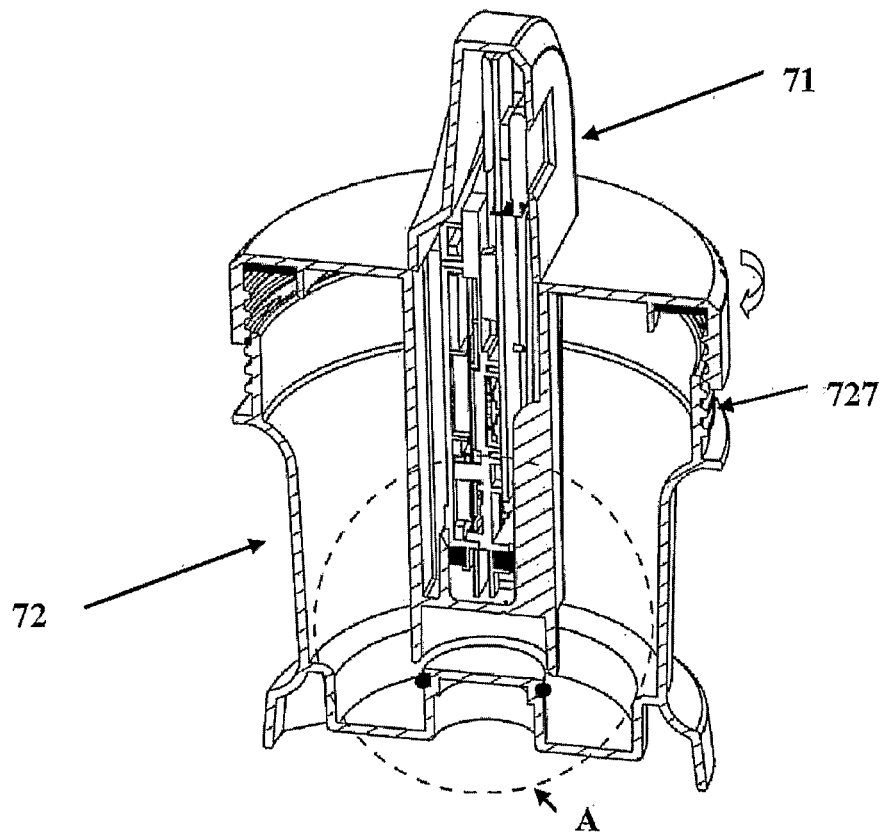
FIG. 13 is a section view of the structure of the detecting device shown in FIG. 4 when it is inserted into the collecting chamber, but the piston has not yet been inserted into the transferring chamber.
Figure 14:
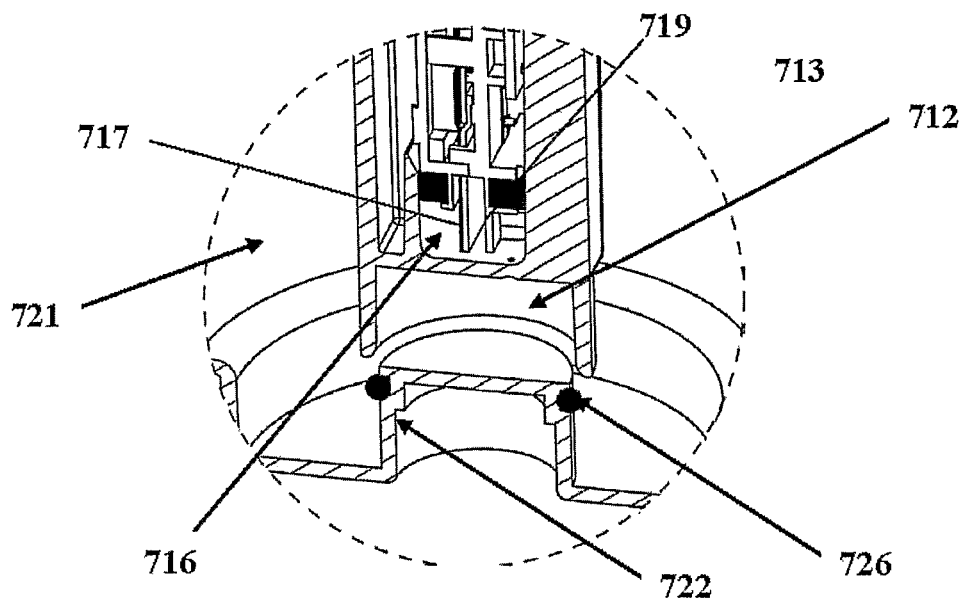
FIG. 14 is a local enlarged view of the structure of A part shown in FIG. 13.

FIGS. 4-16 are some other specific embodiments of the invention. In a specific embodiment, the detection kit 70 comprises a collecting device 72 and a detecting device 71. The collecting device 72 comprises a collecting chamber 721 with one end 723 opened and the other end 724 closed. A protruded piston 722 is disposed within the collecting chamber, on the closed end 724 of the collecting chamber, i.e., the bottom, and is fixed on the bottom, as shown in FIG. 6, with a sealing ring 726 is disposed on the top end of the piston. A detecting device 71 comprises a detecting chamber 716 and a piston chamber or transferring chamber 712, the detecting chamber and a piston chamber share a common wall 7111 whereon two small pores 714 and 713 are disposed to connect the detecting chamber with the piston chamber or transferring chamber, as shown in FIGS. 5 and 7. The small pores are shaped to be a cylinder, as shown in FIG. 10, the two small pores have a diameter of 0.5 millimeter and a depth of 1 millimeter. The piston and the piston chamber are positioned such that when the piston chamber is inserted into the collecting chamber, the piston is just against the piston chamber; the piston and the piston chamber are configured to have a height and a depth such that the piston can be inserted into the piston chamber completely; and the piston and the piston chamber are also configured to have diameters such that the piston 722 can be rightly inserted into the piston chamber 712 while the piston can seal an opening 715 of the piston chamber very well. In this embodiment, the detecting chamber 716, the piston chamber or transferring chamber 712, and their commonly shared wall 7111 are made of plastic materials and are directly injection molded as one piece; the collecting chamber 721, bottom and protruded piston 722 are made of plastic materials and are injection molded as one piece. In some other specific embodiments, the piston and the collecting chamber can of course be incorporated while manufacturing, or manufactured separately and then adhered together by means such as glue. The detecting chamber and the piston chamber or transferring chamber can also be manufactured separately and connected subsequently, with a layer of the film of small pores disposed therebetween to separate the detecting chamber and the piston chamber or transferring chamber. When in use, the detecting device 71 is inserted into the collecting chamber 721, the liquid inside the collecting chamber then enters the piston chamber or transferring chamber 712 via the opening 715, while the piston is not yet inserted into the piston chamber or transferring chamber at this time. At this time, the air inside the piston chamber is expelled out through the small pores of the film. Due to the liquid surface tension at these small pores, the liquid inside the piston chamber or transferring chamber cannot get into the detecting chamber via the small pores, as shown in FIGS. 13 and 14. When the piston is further inserted into the piston chamber, the pressure inside the piston chamber or transferring chamber is increased by the piston such that it can break the liquid surface tension at the small pores to force the liquid sample to get into the detecting chamber, as shown in FIGS. 15 and 16.

Figure 8:
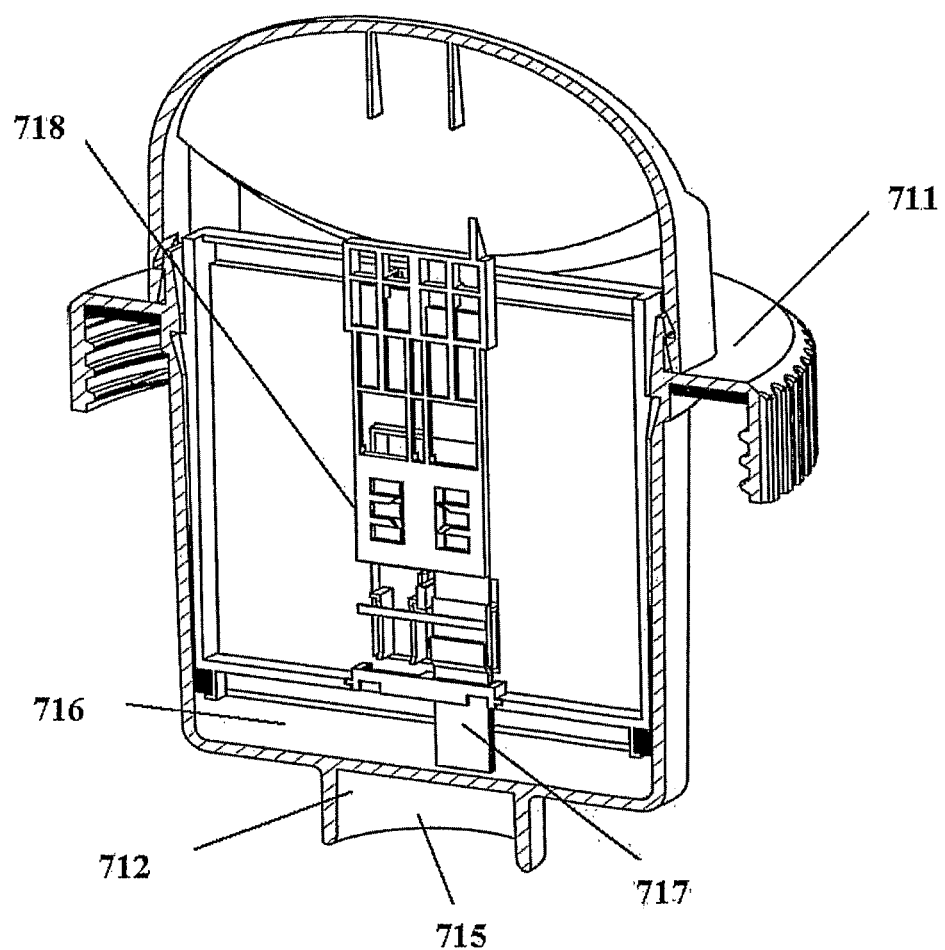
FIG. 8 is a section view of the structure of the detecting device shown by FIG. 7.
Figure 9:
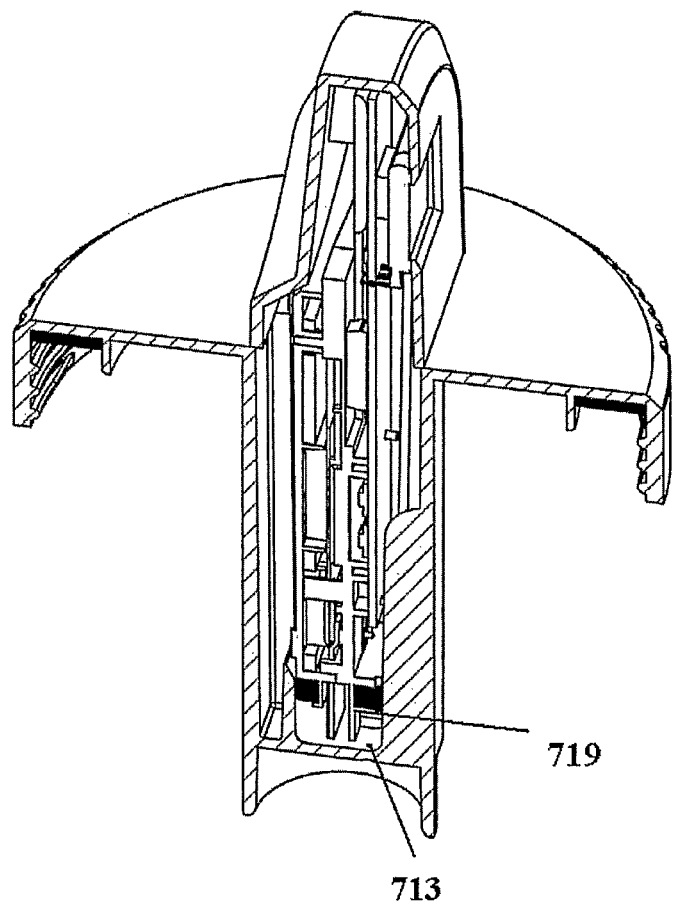
FIG. 9 is another section view of the structure of the detecting device shown by FIG. 7.

The detecting chamber can further comprise a detecting element 717 and a reading device 718 to read the detecting results of the detecting element, the reading device displays the result directly on a LCD displayer 710, as shown in FIG. 8. When the liquid sample enters the detecting chamber, the detecting element contacts the liquid sample and reacts to obtain detecting result, and to display the detecting result directly on the LCD displayers through the reading device. The specific embodiments about the detecting elements and reading devices disclosed in Chinese applications for a patent for invention such as CN200410045273.4, CN200410045275.3, and CN200410063910.1 can be used in the present invention to detect an analyte in a liquid sample and read the testing results of the detecting element.

Figure 15:
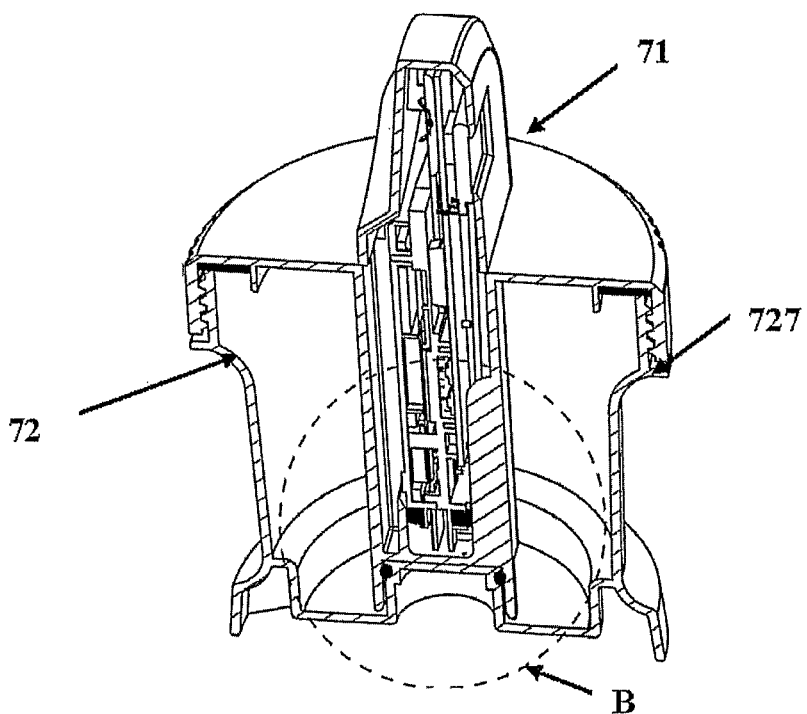
FIG. 15 is a section view of the structure of the device showing that the piston moves into the transferring chamber and forces the liquid sample to enter the detecting chamber via pore 713 after it seals the liquid channel of the transferring chamber, as shown in FIG. 14.
Figure 16:
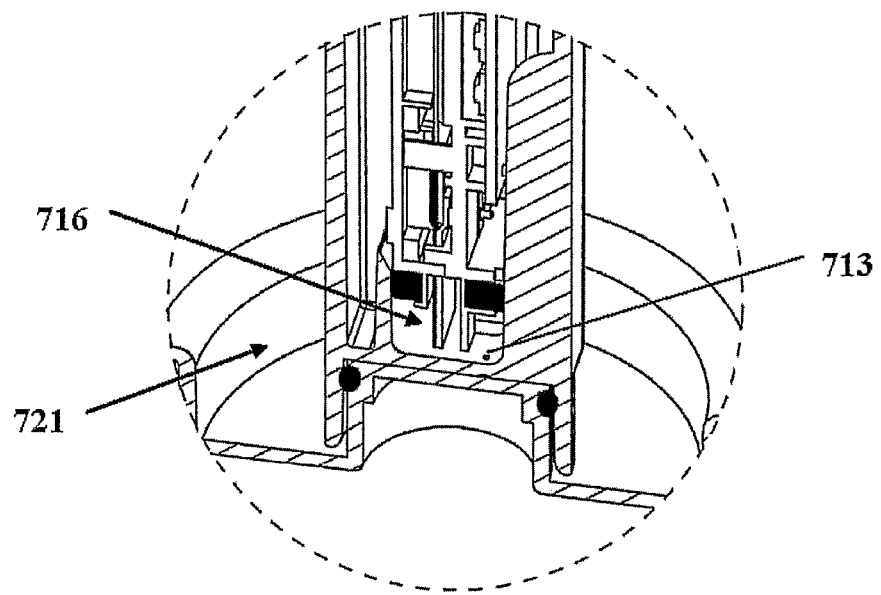
FIG. 16 is an enlarged view of the structure of B part shown in FIG. 15.

In a more preferable specific embodiment, detecting chamber 716, piston chamber or transferring chamber 712 and a lid 711 for covering the opening of the collecting chamber are further connected as one piece, as shown in FIG. 8 and FIGS. 13-16. The collecting chamber and the lid have screw threads 727, separately. When the lid is covered onto the opening of the collecting chamber, rotating the lid to move the lid from a high position to a low position, the detecting chamber and the transferring chamber connected with the lid are correspondingly also lowered from a high position to a low position, thus completing the sampling and transferring of the liquid sample, as shown in FIGS. 13-16. When the lid is covered onto the collecting chamber opening on the collecting device, the piston chamber connected with the lid is also inserted into the collecting chamber, and the liquid sample in the collecting chamber enters the piston chamber 712 via the piston chamber opening 715, and the air in the piston chamber is expelled into the detecting chamber. When the lid further rotating, the lid can move a distance that is the same as the height of the piston; thereby, when the lid seals the opening of the collecting chamber, as shown in FIG. 15, the piston fills the entire piston chamber and forces almost all the liquid inside the piston chamber to enter the detecting chamber via the small pores.

In some cases, the liquid sample coming out from the small pores enters the detecting chamber by "spraying", sometimes due to the continuance and impermanency of the operation of sampling. To prevent the liquid sample from spraying onto other elements in the detecting chamber, a protecting element is disposed above the small pores. Such an element prevents the liquid from spraying onto other elements while does not influence contact between the liquid sample and the detecting element. As shown in FIG. 14, an inverse "U" shape or inverse "⊥" shape structure is disposed above the small pores. Such a structure makes the liquid sample in "spraying" form enters the detecting chamber slowly so that it can contact the detecting element without spraying onto other element. Especially when the detecting chamber contains electronic element, using the above protective structure will protect functions of the electronic element from being damaged because of being contaminated by the liquid sample, and keep the electronic element safe.

In some other preferable embodiments, when the liquid surface tension at the small pores is configured through the sizes, shapes or depths of the pores, it is better to keep the inner surfaces 2003, 7113 of the small pores dry before the detecting device is inserted into the collecting chamber to obtain an ideal surface tension. Specifically, tests have shown that when the inner surface of the small pores is covered with a layer of water molecules, the surface tension generated between the liquid and air at the small pores may be reduced. In addition, in order to obtain better effect, the detecting device is configured disposable without repeated use.

FIG. 3 exhibits some other specific embodiments of the invention. In a specific embodiment, the collecting device 50 provided by the invention comprises a liquid sample collecting chamber 101, and the piston chamber 501 is located at the bottom of the collecting chamber, as shown in FIG. 3A. A detecting device 60 comprises a detecting chamber 601 with one end having an opening and the other end is sealed by a film 209 having small pores. In a specific embodiment, the bottom end 604 of the detecting chamber comprises two small pores 602, 603. The entire detecting chamber is a cylinder; the end 604 comprising small pores and the opening 503 of the piston chamber can cooperate to seal the piston chamber 501, as shown in FIG. 3B. The entire detecting chamber and its end having small pores are made of plastic materials and are injection molded as one piece. Piston chamber 501 is eventually a transferring chamber, too. During application, when the liquid sample is collected into the collecting chamber, it enters piston chamber 501 via the opening end 503 of the piston, i.e., the liquid channel of the transferring chamber. When the detecting chamber is inserted into the collecting chamber, the bottom end 604 of the detecting chamber contacts the liquid sample first. Although there are two small pores at the bottom end 604 of the detecting chamber, these small pores are configured to have special shape or size, such as an inner diameter of 0.3 millimeter, the surface tension generated by these small pores is sufficient to prevent the liquid sample in the collecting chamber from entering the detecting chamber. Even if the bottom end 604 of the detecting chamber is lower than the liquid surface level of the collecting chamber, i.e., there is a level difference, the liquid surface tension at the small pores still can prevent the liquid sample in the collecting chamber from entering the detecting chamber, as shown in FIG. 3C. When the detecting chamber moves further, the bottom end 604 of the detecting chamber having small pores seals the opening 503 of the piston chamber, thereby preventing the liquid in collecting chamber 101 from entering the detecting chamber 501, and maintaining the volume of the liquid sample in the piston chamber to achieve the purpose of sampling quantitatively. At this time, it is still possible to not allow the liquid sample in the piston chamber entering the detecting chamber via the small pores, and the piston is at the so-called first position. During the process that the piston moves from the first position to a so-called second position, i.e., the piston moves downward continuously, the pressure at the small pores increases and finally breaks the surface tension at the small pores, and the liquid sample in the piston chamber enters the detecting chamber 601 via small pores 602, 603, as shown in FIG. 3C. In the detecting chamber, reaction occurs between sample and the detecting element in the detecting chamber.

The other aspect of the invention provides a method for detecting whether the sample contains the analyte, which comprises inserting a detecting device into a liquid sample collecting chamber; allowing the liquid sample in the collecting chamber to enter a liquid sample transferring chamber of the detecting device via a liquid channel, but not allowing the liquid to enter a detecting chamber via a film of small pores disposed between the detecting chamber and the transferring chamber; inserting a piston into the liquid sample transferring chamber to force the liquid sample in the transferring chamber to enter the detecting chamber via the film of small pores disposed between the detecting chamber and the transferring chamber. More specifically, as shown in FIG. 1, a detecting device 20 is inserted into a liquid sample collecting chamber 101 wherein the liquid sample enters the liquid sample transferring chamber 201; at this time, the liquid sample cannot enter the detecting chamber via the film of small pores 209 disposed between the detecting chamber 202 and the transferring chamber 201; piston 102 is inserted into the transferring chamber 201 to force a part of liquid sample to enter the detecting chamber via the film of small pores 209. FIGS. 4-16 show a specific embodiment, wherein the detecting method comprises providing a detecting device 71 comprising a detecting chamber 716, a transferring chamber 712, and a plastic film 7111 having small pores 713, 714 disposed between the detecting chamber and the transferring chamber, the small pores are configured to have an inner diameter of 0.5 millimeter and a height of 1.5 millimeter, as shown in FIG. 10; providing a collecting device 702 comprising a collecting chamber 721 and a piston 722 located inside the collecting chamber, the piston protrudes upwardly from the bottom 724 of the collecting chamber; inserting the detecting device into the collecting chamber such that the liquid inside the collecting chamber enters the transferring chamber 712 via the liquid channel 715, and the piston seals the liquid channel of the transferring chamber and the collecting chamber, the piston is at a first position in the transferring chamber, at this time the liquid sample cannot enter the detecting chamber from the transferring chamber via the film of the small pores; inserting the piston into the transferring chamber and moving from the first position to a second position to force the liquid sample to enter the detecting chamber from the transferring chamber via the film of small pores; moving the piston until it cannot move, and almost all the liquid sample in the transferring chamber are forced to enter the detecting chamber.

In some other specific embodiments, after the piston is inserted into the transferring chamber and forces the liquid sample to enter the detecting chamber via the small pores, the piston is not allowed to move back relative to the transferring chamber. For example, after the piston chamber moves upwardly, relative to piston, and forces the liquid sample in the piston chamber to enter the detecting chamber via the small pores by rotating the lid clockwise, the lid no longer can be rotated counter clockwise, which will prevent the liquid sample entering the detecting chamber from refluxing into the transferring chamber to possibly contaminate the liquid sample in the collecting chamber.

The "sample" in the present invention refers to any substance needs to be determined whether it contains an analyte and/or its concentration thereof, or substances wherein one or more samples need to be determined whether containing an analyte and/or its amount, or substances that simply need to be evaluated qualitatively. The sample can be a liquid specimen including body fluids such as blood, serum, plasma, saliva, urine, tears, sperm and marrow; the liquid specimen can also be water, such as water from sea, lake, river and the like or home-use water, city water or sources of industrial water, runoff water or sewage; the sample can also be food sample such as milk and wine. Phlegm, semi-solid or solid samples can be used to prepare samples of liquid, lavage fluid, suspension fluid or extracted fluid. For example, samples of throat or genitalia can be impregnated in liquid to make a sample. The sample can be a mixture of liquid, solid and gas, or any related mixtures such cell suspension liquid in a diluted liquid or solution. Samples include biological materials such as cell, microbes, cell organelle and biological complexes. Liquid samples can be prepared from soil, dejecta, tissues, organs; biological body fluid or other non-liquid sample in nature such as solid, semi-solid or high adhesive materials. For example, these solid or semi-solid samples can be mixed with suitable solutions such as diluted liquid. Samples can be prepared to form liquid samples by dipping to soft, freezing and de-freezing, or other extracting methods. The remaining particulate materials can be removed with conventional methods such as by using filtering paper or deposit.

The analyte in the present invention refers to "drug of abuse" (DOA) or other interested substances contained in the samples. "Drug of abuse" (DOA) refers to using drugs (typically for paralyzing nerves) not for medical purpose. Abuse of these drugs will damage the body and nerves, to generate dependency, addiction and/or death. Examples of drug of abuse include cocain, amphetamine (such as black beauties, white amphetamine tablets, dexamphetamine, dextro-amphetamine, Beans); methamphetamine (crank, methamphetamine, crystal, speed); barbiturate (such as Valium, Roche pharmaceuticals, Nutley, N.J.); ataractic (drugs for assisting sleeping); lysergic acid diethylamide (LSD); depressor (downers, goofballs, barbs, blue devils, yellow jackets, methaqualone); tricyclic antidepressants for depression (TCA, i.e., imipramine, amitriptyline, and doxepin); phencyclidine (PCP), tetrahydrocannabinol (THC, pot, dope, hash, weed, and etc); opiates (i.e., morphia, opium, codeini, heroin, oxycodone); antianxiety drug and sedative-hypnotic drugs, antianxiety drug is mainly for reducing anxiety, tension, fears and stabilizing emotion as well as sedative-hypnotic, including benzodiazepines (BZ), non-typical BZs, fused-dinitrogen-NB23Cs, benzepins, ligands of BZ acceptors, ring-opening BZs, diphenylmethane derivatives, piperazinecarboxylates, piperidinecarboxylates, quinazoline ketones, thiazine and thiazole derivatives, other heterocyclics, sedative/anodyne of imidazole type, propylene glycol derivatives—carbamates, aliphatic compounds, and anthracene derivatives. The device can also be used to detect drugs which are for medical purpose but is easily overdose such as tricyclic antidepressants (imipramine or analogs) and acetaminophen. These drugs will be decomposed to different small molecules after absorbed by human body, and these small molecules are present in body fluids such as blood, urine, saliva, and perspiration.

EXAMPLES

For better understanding the invention, examples are provided herewith for further illustration. These examples are only for the purpose of illustrating the effects and manners of specific embodiments of the present invention, they should in no circumstance be interpreted to limit the scope of the present invention.

Example 1

Variations of the Sampling Amount of the Detection Device

This experiment is explained by combining FIGS. 4-7, 17, and 13-16. The experiment uses a detection device having a structure shown in FIGS. 4-7. FIG. 7 shows that the plastic sheet between the detecting chamber 716 and the transferring chamber 712 does not have two small pores but one hole of a diameter of 7 millimeter, and the hole is adhered with a round hydrophobic porous film having a thickness of 10 millimeter; the sectional view of the hole is shown in FIG. 17. Such a film is purchased from AHLSTROM FILTRATION LLC (www.ahlstrom.com, addressed at 42431-0030, Kentucky State, U.S.A., http://www.ahlstrom.com, telephone (270), 8221-0140; Fax: (270), 326-3290, post box 1410). The porous film used in the experiment has a batch No. 0256, a thickness of 16.5 microns, a lateral stretching strength of 86.0 lb/inch, a longitudinal stretching strength of 78.0 lb/inch; a gas permeability rate (CFM) of 256.0 cubic inch/minute/square inch; the material is a polyester membrane, and it pore sizes are about 8 millimeters.

The collecting chamber contains urine in amounts of 55, 70, 80, 90 and 105 liters, respectively (shown under section A of the table). Different persons operate according to the process shown in FIGS. 13-16, repeating 41, 40, 41, 39 and 29 times, respectively. Each repeating is operated according to the following steps: 1. put a collecting cup 72 on a horizontal plane; 2. align the remark lines of the edge of the transparent cup and the lid (not shown) and insert the detecting device 71 gently into the transparent cup, and to rotate the lid clockwise till fastened; 3. measure the volume of the urine entering the detecting chamber. Please note that the lid should not be unscrewed as long as it has been inserted into the transparent cup.

Finally, measure the different urine volumes (shown under section B of the table) entering the detecting chamber of the collecting cup 72. The results are recorded in the following table. It can be seen from the table that, using the device of the present invention, variations of the volumes of the urine samples in the collecting cup does not significantly influence liquid volumes entering the detecting chamber. Of the 181 times operations, the urine volumes in the detecting chamber are between 1.5 and 2.9 millimeters in 177 operations; thus, there are only four operations having invalid volumes, since our experiment has already shown that THC detecting result cannot be correctly obtain if the sample volume in the detecting chamber is less than 1.5 millimeter or greater than 3.0 millimeter. This is a conclusion if we consider the variation of liquid volume in the detecting chamber as the only variable parameter in detecting the THC in the sample.

Of course liquid volume entering the detecting chamber can be adjusted by selecting the film of small pores having different parameters if the analyte to be detected is other than THC. For example, the volume can be maintained between 4 and 5 milliliters, 6 and 7 milliliters, or 1 and 2.5 milliliters.

TABLE 1

The impact of different urine volumes in the collecting chamber to the volumes entering the detecting chamber

| A | B |
|---|---|
| 55 ml | 2.2 |
| 55 ml | 2.3 |
| 55 ml | 2.2 |
| 55 ml | 2.3 |
| 55 ml | 2.3 |
| 55 ml | 2.1 |
| 55 ml | <u>4.1</u> |
| 55 ml | 2.3 |
| 55 ml | 2.3 |
| 55 ml | 2.4 |
| 55 ml | 1.8 |
| 55 ml | 2.1 |
| 55 ml | 2.2 |
| 55 ml | 2.3 |
| 55 ml | 2.1 |
| 55 ml | <u>0.9</u> |
| 55 ml | 2.4 |
| 55 ml | 2.3 |
| 55 ml | 2.2 |
| 55 ml | 2.3 |
| 55 ml | 1.7 |
| 55 ml | 1.8 |
| 55 ml | 2.3 |
| 55 ml | 2.4 |
| 55 ml | 1.6 |
| 55 ml | 2.2 |
| 55 ml | 2.4 |
| 55 ml | 2.5 |
| 55 ml | 2.4 |
| 55 ml | 2.2 |
| 55 ml | <u>0.6</u> |
| 55 ml | 2.8 |
| 55 ml | 2.3 |
| 55 ml | 2.2 |
| 55 ml | 2.2 |
| 55 ml | 2.2 |
| 55 ml | 2.1 |
| 55 ml | 2.4 |
| 55 ml | 2.4 |
| 55 ml | 2.3 |
| 55 ml | 2.1 |

TABLE 1-continued

The impact of different urine volumes in the collecting chamber to the volumes entering the detecting chamber

| A | B |
|---|---|
| 70 ml | 2.2 |
| 70 ml | 2.2 |
| 70 ml | 2.2 |
| 70 ml | 3.0 |
| 70 ml | 2.0 |
| 70 ml | 2.0 |
| 70 ml | 2.2 |
| 70 ml | 2.0 |
| 70 ml | 2.2 |
| 70 ml | 2.2 |
| 70 ml | 2.3 |
| 70 ml | 2.4 |
| 70 ml | 2.4 |
| 70 ml | 2.2 |
| 70 ml | 2.4 |
| 70 ml | 2.2 |
| 70 ml | 2.4 |
| 70 ml | 2.0 |
| 70 ml | 2.3 |
| 70 ml | 2.2 |
| 70 ml | 2.2 |
| 70 ml | 2.3 |
| 70 ml | 2.4 |
| 70 ml | 1.4 |
| 70 ml | 2.4 |
| 70 ml | 2.4 |
| 70 ml | 2.1 |
| 70 ml | 2.3 |
| 70 ml | 2.2 |
| 70 ml | 2.0 |
| 70 ml | 2.4 |
| 70 ml | 2.3 |
| 70 ml | 1.9 |
| 70 ml | 2.2 |
| 70 ml | 2.2 |
| 70 ml | 2.3 |
| 70 ml | 2.3 |
| 70 ml | 1.9 |
| 70 ml | 2.3 |
| 70 ml | 2.2 |
| 80 ml | 2.3 |
| 80 ml | 2.3 |
| 80 ml | 2.2 |
| 80 ml | 2.3 |
| 80 ml | 2.1 |
| 80 ml | 2.2 |
| 80 ml | 2.2 |
| 80 ml | 2.2 |
| 80 ml | 2.3 |
| 80 ml | 2.2 |
| 80 ml | 2.2 |
| 80 ml | 2.2 |
| 80 ml | 2.2 |
| 80 ml | 2.6 |
| 80 ml | 2.3 |
| 80 ml | 2.3 |
| 80 ml | 2.2 |
| 80 ml | 2.3 |
| 80 ml | 2.0 |
| 80 ml | 2.2 |
| 80 ml | 2.3 |
| 80 ml | 2.1 |
| 80 ml | 2.2 |
| 80 ml | 2.2 |
| 80 ml | 2.4 |
| 80 ml | 2.2 |
| 80 ml | 2.2 |
| 80 ml | 2.3 |
| 80 ml | 2.2 |
| 80 ml | 2.2 |
| 80 ml | 2.5 |
| 80 ml | 2.2 |
| 80 ml | 2.3 |
| 80 ml | 2.4 |
| 80 ml | 1.0 |
| 80 ml | 2.3 |
| 80 ml | 2.2 |
| 80 ml | 3.0 |
| 80 ml | 2.3 |
| 80 ml | 2.4 |
| 90 ml | 2.3 |
| 90 ml | 2.2 |
| 90 ml | 2.3 |
| 90 ml | 2.3 |
| 90 ml | 2.4 |
| 90 ml | 2.3 |
| 90 ml | 2.2 |
| 90 ml | 2.3 |
| 90 ml | 2.0 |
| 90 ml | 2.2 |
| 90 ml | 2.3 |
| 90 ml | 2.2 |
| 90 ml | 2.4 |
| 90 ml | 2.1 |
| 90 ml | 2.2 |
| 90 ml | 2.4 |
| 90 ml | 2.2 |
| 90 ml | 2.1 |
| 90 ml | 2.3 |
| 90 ml | 2.3 |
| 90 ml | 2.2 |
| 90 ml | 2.0 |
| 90 ml | 2.2 |
| 90 ml | 2.3 |
| 90 ml | 2.2 |
| 90 ml | 2.3 |
| 90 ml | 2.1 |
| 90 ml | 2.4 |
| 90 ml | 3.0 |
| 90 ml | 2.0 |
| 105 ml | 2.2 |
| 105 ml | 2.2 |
| 105 ml | 2.4 |
| 105 ml | 2.2 |
| 105 ml | 2.3 |
| 105 ml | 2.2 |
| 105 ml | 2.3 |
| 105 ml | 2.2 |
| 105 ml | 2.0 |
| 105 ml | 2.3 |
| 105 ml | 2.4 |
| 105 ml | 2.0 |
| 105 ml | 2.3 |
| 105 ml | 2.4 |
| 105 ml | 2.4 |
| 105 ml | 2.4 |
| 105 ml | 2.6 |
| 105 ml | 2.2 |
| 105 ml | 2.2 |
| 105 ml | 2.2 |
| 105 ml | 2.8 |
| 105 ml | 2.0 |
| 105 ml | 2.2 |
| 105 ml | 2.3 |
| 105 ml | 2.3 |
| 105 ml | 2.2 |
| 105 ml | 2.4 |
| 105 ml | 2.0 |
| 105 ml | 2.3 |

The invention claimed is:
1. A detection device for analyzing an analyte in a liquid sample, comprising:
  a) a detecting chamber for accepting a detecting element,
  b) a liquid sample transferring chamber,
  c) a film of small pores disposed between the detecting chamber and the liquid sample transferring chamber, wherein when the detection device is inserted into a liquid sample collecting chamber, liquid sample in the collecting chamber enters the liquid sample transferring chamber, but the liquid sample cannot enter the detecting chamber via said film of small pores, d) a piston disposed in the liquid sample transferring chamber, the piston being movable between a first position and a second position, wherein movement of the piston from the first position to the second position forces a part of liquid sample in the transferring chamber to enter the detecting chamber through said film of small pores, wherein when the piston is in the first position the piston prevents flow of the liquid sample from the liquid sample collecting chamber into the liquid sample transferring chamber, and wherein when the piston is in the first position, flow of the liquid sample from the liquid sample transferring chamber to the detection chamber is prevented by the film of small pores while flow of gas from the liquid sample transferring chamber to the detection chamber is not prevented, and e) a protecting element disposed adjacent the film of small pores operable to block spray of liquid sample through the small pores.

2. The device according to claim 1, wherein the small pores of said film are so configured that the liquid surface tension at the pores prevents the liquid sample freely enters the detecting chamber; when the pressure difference between the transferring chamber and the detecting chamber is less than or equal to the liquid surface tension at the small pores, the liquid sample in the transferring chamber cannot enter the detecting chamber via the small pores, and when the pressure difference between the transferring chamber and the detecting chamber is greater than the liquid surface tension at the small pores, the liquid sample in the transferring chamber can enter the detecting chamber via the small pores.

3. The device according to claim 2, wherein a piston moving inside the transferring chamber increases the inside pressure to that greater than the liquid surface tension at the small pores.

4. The device according to claim 1, wherein a liquid channel allowing liquid to freely pass through is provided between the liquid sample transferring chamber and the collecting chamber, said liquid channel is sealed by the piston after a part of liquid sample flows from the collecting chamber into the transferring chamber via the channel.

5. The device according to claim 4, wherein the small pores are so configured that the pressure inside the transferring chamber is less than or equal to the liquid surface tension at the small pores when the piston seals the liquid channel.

6. The device according to claim 4, wherein the piston has a first position and a second position in the transferring chamber; when at the first position, the piston seals the liquid channel, and the transferring chamber contains a part of liquid sample that comes from the collecting chamber, but the liquid sample cannot enter the detecting chamber via the film of small pores; when moving from the first position to the second position, the piston allows the liquid sample to enter the detecting chamber via the film small pores.

7. The device according to claim 1, wherein the piston is located in the liquid sample collecting chamber.

8. The device according to claim 1, wherein the transferring chamber and the detecting chamber are connected as one piece.

9. The device according to claim 1, wherein the transferring chamber, the detecting chamber, and the film of small pores are constructed as one piece through injection molding.

10. The device according to claim 1, wherein the film contains one or more small pores.

11. The device according to claim 1, wherein the small pores of the film have diameters between 0.1 and 5 millimeters.

12. The device according to claim 1, wherein the device further comprises a detecting element disposed inside the detecting chamber.

13. The device according to claim 12, wherein the device further comprises a reading device for reading the testing result from the detecting element.

14. The device according to claim 12, wherein the detecting element is a lateral flow reagent strip.

15. The device according to claim 1, wherein the film of small pores is a hydrophobic film.

16. The device according to claim 15, wherein the small pores have pore sizes between 0.1 and 100 microns.

17. The device according to claim 15, wherein the hydrophobic film of small pores comprises a hydrophilic film whereon hydrophobic reagent is treated.

18. The device according to claim 15, wherein the hydrophobic film of small pores comprises glass fibers, polyester film, or acetic fiber film.

19. The device according to claim 15, wherein the hydrophobic film of small pores has a gas permeating rate of 10-800 cubic inches/minute/square inch.

* * * * *